US011443843B2

(12) United States Patent
Govindjee et al.

(10) Patent No.: US 11,443,843 B2
(45) Date of Patent: Sep. 13, 2022

(54) PERSONAL CUSTOMIZED GUIDANCE FOR TREATING PATIENTS

(71) Applicant: International Business Machines Corporation, Armonk, NY (US)

(72) Inventors: Anita Govindjee, Ithaca, NY (US); Kai Liu, Malden, MA (US); Su Liu, Austin, TX (US); Manjunath Ravi, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 461 days.

(21) Appl. No.: 16/240,080

(22) Filed: Jan. 4, 2019

(65) Prior Publication Data
US 2020/0219605 A1 Jul. 9, 2020

(51) Int. Cl.
G16H 20/60 (2018.01)
G16H 10/60 (2018.01)
G16H 80/00 (2018.01)
G16H 50/20 (2018.01)
G16H 50/30 (2018.01)

(52) U.S. Cl.
CPC ............ G16H 20/60 (2018.01); G16H 10/60 (2018.01); G16H 50/20 (2018.01); G16H 80/00 (2018.01); G16H 50/30 (2018.01)

(58) Field of Classification Search
USPC ........................................................ 705/2–3
See application file for complete search history.

(56) References Cited

U.S. PATENT DOCUMENTS 6,754,655 B1 * 6/2004 Segal .................... G06F 40/295
7,879,794 B2 2/2011 Weyer et al.
(Continued)

FOREIGN PATENT DOCUMENTS

WO 2009/065845 A1 5/2009
WO 2010/070645 A1 6/2010

OTHER PUBLICATIONS

Freedman, et al., "Association between smoking and risk of bladder cancer among men and women", American Medical Association, JAMA, Aug. 17, 2011, vol. 306, No. 7 pp. 737-745. (Year: 2011).*
(Continued)

*Primary Examiner* — Amber A Misiaszek
(74) *Attorney, Agent, or Firm* — Scott S. Dobson; Madeline F. Schiesser; Keohane & D'Alessandro, PLLC

(57) ABSTRACT

Approaches presented herein enable treating a medical condition via individual customized cognitive guidance. More specifically, a current interactive and customized diagnosis object (ICDO) comprising a treatment schedule for a patient is generated by combining a set of previous ICDOs from the patient, wherein each ICDO has a structure which defines elements that are used to diagnose a symptom and match the patient with a treatment. A status of the patient is monitored in real time via an internet of things network to detect an actual event of the patient differing from the treatment schedule. In real time, the treatment schedule is modified responsive to the differing event by adjusting the current ICDO by exchanging one element of the treatment plan for a new element according to a learned set of rules to compensate for the differing event. This modified treatment schedule is provided to the patient in real time.

20 Claims, 6 Drawing Sheets

(56) References Cited

U.S. PATENT DOCUMENTS

| | | | |
|---|---|---|---|
| 8,318,813 B2 | 11/2012 | Sanfilippo | |
| 9,521,973 B1* | 12/2016 | Beiski | A61B 5/168 |
| 9,524,654 B2 | 12/2016 | Simons-Nikolova et al. | |
| 2002/0049615 A1* | 4/2002 | Huber | G16H 40/67 |
| | | | 705/3 |
| 2002/0138304 A1* | 9/2002 | Fontanesi | G06Q 10/10 |
| | | | 705/2 |
| 2003/0055679 A1* | 3/2003 | Soll | G16H 80/00 |
| | | | 705/2 |
| 2003/0115248 A1 | 6/2003 | Kitada et al. | |
| 2005/0021240 A1* | 1/2005 | Berlin | G16H 50/20 |
| | | | 702/20 |
| 2013/0195827 A1 | 8/2013 | Blum et al. | |
| 2016/0012194 A1 | 1/2016 | Prakash et al. | |
| 2016/0117952 A1 | 4/2016 | Simons-Nikolova et al. | |
| 2016/0140864 A1 | 5/2016 | Forman et al. | |
| 2016/0188807 A1 | 6/2016 | Heywood et al. | |
| 2017/0220772 A1 | 8/2017 | Vleugels et al. | |
| 2017/0235909 A1* | 8/2017 | Lozano | G16H 40/20 |
| | | | 705/3 |
| 2017/0344722 A1 | 11/2017 | Ashoori et al. | |

OTHER PUBLICATIONS

Baril, et al., "The Use of Activity Monitoring and Machine Learning for the Functional Classification of Heart Failure", University of Toronto (Canada), pp. 1-203, 2018 (Year: 2018).*

* cited by examiner

PERSONAL CUSTOMIZED GUIDANCE FOR TREATING PATIENTS

TECHNICAL FIELD

The present invention relates generally to cognitive modeling and, more specifically, to treating an outpatient via an individual customized cognitive data object.

BACKGROUND

Many people visit their doctor at least once a year, whether for an annual physical or for another medical concern. However, patients generally meet with their doctor for only a limited period of time during an office visit, and the doctor is limited in what he or she can do for the patient during such a short time period. Moreover, a patient may be unable or reluctant to discuss all of his or her concerns and medical issues with a doctor, making it hard to diagnose a medical issue and to find a proper treatment. Furthermore, while a doctor may prescribe a therapy to treat a medical issue, it is up to the patient to make sure that this therapy is continuously followed. This can be a difficult task for a patient, particularly if the nature of the patient's medical issue makes adhering to a scheduled therapy a seemingly herculean task. Moreover, doctor's offices, particularly specialists, often schedule appointment weeks, if not months, in advance. This can result in a therapy being tuned to a patient at a slow rate, through a seemingly endless cycle of appointments and small adjustments across several months. As such, the time needed to find an optimum therapy for a patient can be measured in years, which is often frustrating for patients struggling daily with a medical condition. Complicating this matter is the common failure of patients to follow through on their therapy when not under the direct supervision of a doctor, resulting in untreated medical ailments and an inability to find successful treatments for the patients.

SUMMARY

Approaches presented herein enable treating a medical condition via individual customized cognitive guidance. More specifically, a current interactive and customized diagnosis object (ICDO) comprising a treatment schedule for a patient is generated by combining a set of previous ICDOs from the patient, wherein each ICDO has a structure which defines elements that are used to diagnose a symptom of the patient and match the patient with a treatment. A status of the patient is monitored in real time via an internet of things network associated with the patient to detect an actual event of the patient differing from the treatment schedule. In real time, the treatment schedule is modified responsive to the differing event by adjusting the current ICDO of the patient by exchanging one element of the treatment plan for a new element according to a learned set of rules to compensate for the differing event. This modified treatment schedule is provided to the patient in real time.

One aspect of the present invention includes a method for treating a medical condition via individual customized cognitive guidance, the method comprising: generating a current interactive and customized diagnosis object (ICDO) comprising a treatment schedule for a patient by combining a set of previous ICDOs from the patient, wherein each ICDO has a structure which defines elements that are used to diagnose a symptom of the patient and match the patient with a treatment; monitoring a status of the patient in real time via an internet of things network associated with the patient to detect an actual event of the patient differing from the treatment schedule; modifying, in real time, the treatment schedule responsive to the differing event by adjusting the current ICDO of the patient according to a learned set of rules to compensate for the differing event, the adjusting comprising exchanging one element of the treatment plan for a new element; and providing the modified treatment schedule to the patient in real time.

Another aspect of the present invention includes a computer system for treating a medical condition via individual customized cognitive guidance, the computer system comprising: a memory medium comprising program instructions; a bus coupled to the memory medium; and a processor, for executing the program instructions, coupled to a cognitive and customized assistant engine via the bus that when executing the program instructions causes the system to: generate a current interactive and customized diagnosis object (ICDO) comprising a treatment schedule for a patient by combining a set of previous ICDOs from the patient, wherein each ICDO has a structure which defines elements that are used to diagnose a symptom of the patient and match the patient with a treatment; monitor a status of the patient in real time via an internet of things network associated with the patient to detect an actual event of the patient differing from the treatment schedule; modify, in real time, the treatment schedule responsive to the differing event by adjusting the current ICDO of the patient according to a learned set of rules to compensate for the differing event, the adjusting comprising exchanging one element of the treatment plan for a new element; and provide the modified treatment schedule to the patient in real time.

Yet another aspect of the present invention includes a computer program product for treating a medical condition via individual customized cognitive guidance, the computer program product comprising a computer readable hardware storage device, and program instructions stored on the computer readable hardware storage device, to: generate a current interactive and customized diagnosis object (ICDO) comprising a treatment schedule for a patient by combining a set of previous ICDOs from the patient, wherein each ICDO has a structure which defines elements that are used to diagnose a symptom of the patient and match the patient with a treatment; monitor a status of the patient in real time via an internet of things network associated with the patient to detect an actual event of the patient differing from the treatment schedule; modify, in real time, the treatment schedule responsive to the differing event by adjusting the current ICDO of the patient according to a learned set of rules to compensate for the differing event, the adjusting comprising exchanging one element of the treatment plan for a new element; and provide the modified treatment schedule to the patient in real time.

Still yet, any of the components of the present invention could be deployed, managed, serviced, etc., by a service provider who offers to implement passive monitoring in a computer system.

Embodiments of the present invention also provide related systems, methods, and/or program products.

BRIEF DESCRIPTION OF THE SEVERAL VIEWS OF THE DRAWINGS

These and other features of this invention will be more readily understood from the following detailed description of the various aspects of the invention taken in conjunction with the accompanying drawings in which.

Figure 1:
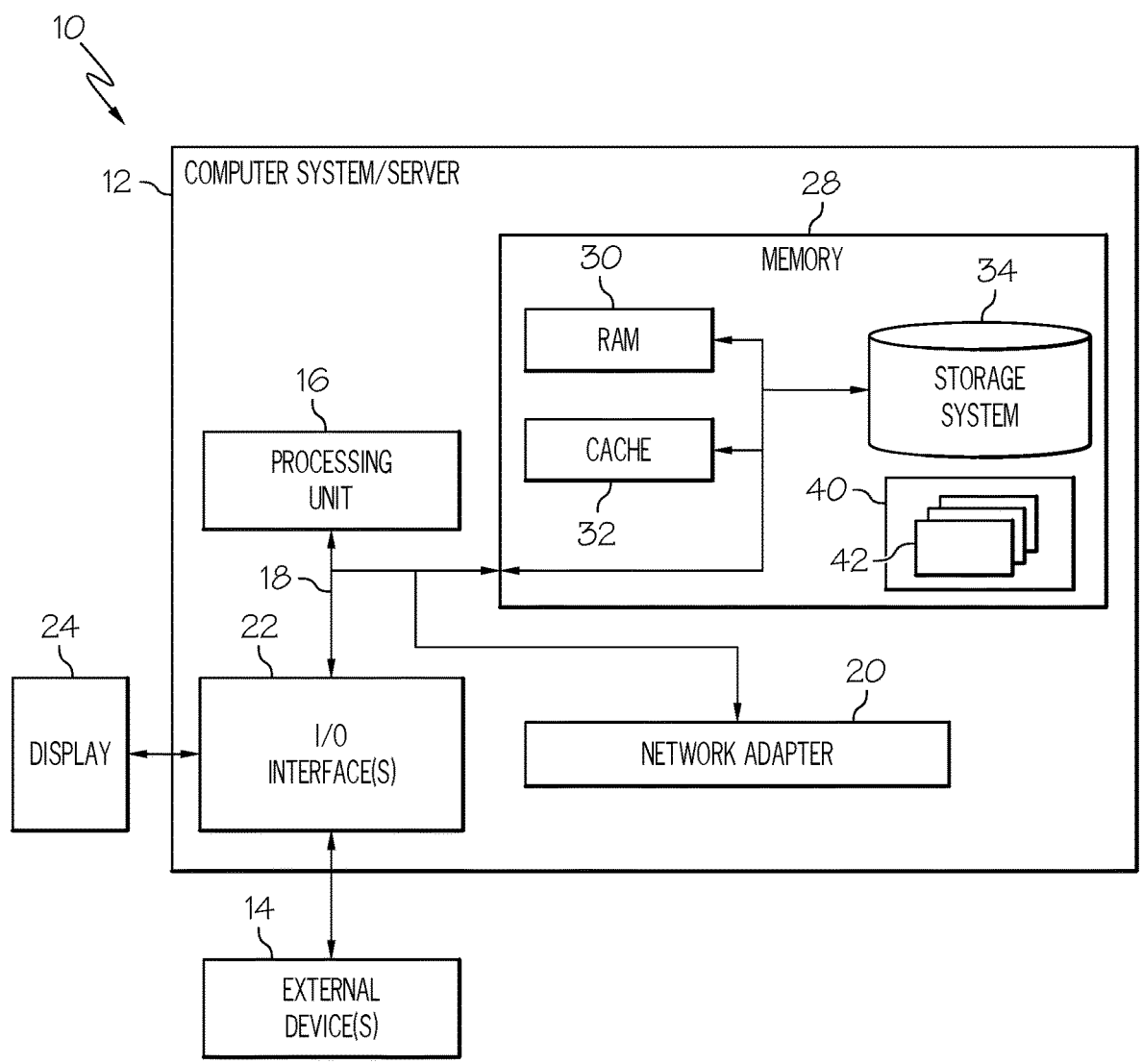
FIG. 1 shows an architecture in which the invention may be implemented according to illustrative embodiments.

The drawings are not necessarily to scale. The drawings are merely representations, not intended to portray specific parameters of the invention. The drawings are intended to depict only typical embodiments of the invention, and therefore should not be considered as limiting in scope. In the drawings, like numbering represents like elements.

DETAILED DESCRIPTION

Illustrative embodiments will now be described more fully herein with reference to the accompanying drawings, in which illustrative embodiments are shown. It will be appreciated that this disclosure may be embodied in many different forms and should not be construed as limited to the illustrative embodiments set forth herein. Rather, these embodiments are provided so that this disclosure will be thorough and complete and will fully convey the scope of this disclosure to those skilled in the art.

Furthermore, the terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. Furthermore, similar elements in different figures may be assigned similar element numbers. It will be further understood that the terms "comprises" and/or "comprising", or "includes" and/or "including", when used in this specification, specify the presence of stated features, regions, integers, steps, operations, elements, and/or components, but do not preclude the presence or addition of one or more other features, regions, integers, steps, operations, elements, components, and/or groups thereof.

Unless specifically stated otherwise, it may be appreciated that terms such as "processing," "detecting," "determining," "evaluating," "receiving," or the like, refer to the action and/or processes of a computer or computing system, or similar electronic data center device, that manipulates and/or transforms data represented as physical quantities (e.g., electronic) within the computing system's registers and/or memories into other data similarly represented as physical quantities within the computing system's memories, registers or other such information storage, transmission or viewing devices. The embodiments are not limited in this context.

As stated above, embodiments described herein provide for treating a medical condition via individual customized cognitive guidance. More specifically, a current interactive and customized diagnosis object (ICDO) comprising a treatment schedule for a patient is generated by combining a set of previous ICDOs from the patient, wherein each ICDO has a structure which defines elements that are used to diagnose a symptom of the patient and match the patient with a treatment. A status of the patient is monitored in real time via an internet of things network associated with the patient to detect an actual event of the patient differing from the treatment schedule. In real time, the treatment schedule is modified responsive to the differing event by adjusting the current ICDO of the patient by exchanging one element of the treatment plan for a new element according to a learned set of rules to compensate for the differing event. This modified treatment schedule is provided to the patient in real time.

Referring now to FIG. 1, a computerized implementation 10 of an embodiment for treating a medical condition via individual customized cognitive guidance will be shown and described. Computerized implementation 10 is only one example of a suitable implementation and is not intended to suggest any limitation as to the scope of use or functionality of embodiments of the invention described herein. Regardless, computerized implementation 10 is capable of being implemented and/or performing any of the functionality set forth hereinabove.

In computerized implementation 10, there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

This is intended to demonstrate, among other things, that the present invention could be implemented within a network environment (e.g., the Internet, a wide area network (WAN), a local area network (LAN), a virtual private network (VPN), etc.), a cloud computing environment, a cellular network, or on a stand-alone computer system. Communication throughout the network can occur via any combination of various types of communication links. For example, the communication links can comprise addressable connections that may utilize any combination of wired and/or wireless transmission methods. Where communications occur via the Internet, connectivity could be provided by conventional TCP/IP sockets-based protocol, and an Internet service provider could be used to establish connectivity to the Internet. Still yet, computer system/server 12 is intended to demonstrate that some or all of the components of implementation 10 could be deployed, managed, serviced, etc., by a service provider who offers to implement, deploy, and/or perform the functions of the present invention for others.

Computer system/server 12 is intended to represent any type of computer system that may be implemented in deploying/realizing the teachings recited herein. Computer system/server 12 may be described in the general context of computer system/server executable instructions, such as program modules, being executed by a computer system. Generally, program modules may include routines, programs, objects, components, logic, data structures, and so on, that perform particular tasks or implement particular abstract data types. In this particular example, computer system/server 12 represents an illustrative system for treating a medical condition via individual customized cognitive guidance. It should be understood that any other computers implemented under the present invention may have different components/software, but can perform similar functions.

Computer system/server 12 in computerized implementation 10 is shown in the form of a general-purpose computing device. The components of computer system/server 12 may include, but are not limited to, one or more processors or processing units 16, a system memory 28, and a bus 18 that couples various system components including system memory 28 to processing unit 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Processing unit 16 refers, generally, to any apparatus that performs logic operations, computational tasks, control functions, etc. A processor may include one or more subsystems, components, and/or other processors. A processor will typically include various logic components that operate using a clock signal to latch data, advance logic states, synchronize computations and logic operations, and/or provide other timing functions. During operation, processing unit 16 collects and routes signals representing inputs and outputs between external devices 14 and input devices (not shown). The signals can be transmitted over a LAN and/or a WAN (e.g., T1, T3, 56 kb, X.25), broadband connections (ISDN, Frame Relay, ATM), wireless links (802.11, Bluetooth, etc.), and so on. In some embodiments, the signals may be encrypted using, for example, trusted key-pair encryption. Different systems may transmit information using different communication pathways, such as Ethernet or wireless networks, direct serial or parallel connections, USB, Firewire®, Bluetooth®, or other proprietary interfaces. (Firewire is a registered trademark of Apple Computer, Inc. Bluetooth is a registered trademark of Bluetooth Special Interest Group (SIG)).

In general, processing unit 16 executes computer program code, such as program code for treating a medical condition via individual customized cognitive guidance, which is stored in memory 28, storage system 34, and/or program/utility 40. While executing computer program code, processing unit 16 can read and/or write data to/from memory 28, storage system 34, and program/utility 40.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media, (e.g., VCRs, DVRs, RAID arrays, USB hard drives, optical disk recorders, flash storage devices, and/or any other data processing and storage elements for storing and/or processing data). By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and/or an optical disk drive for reading from or writing to a removable, non-volatile optical disk such as a CD-ROM, DVD-ROM, or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program code embodied on a computer readable medium may be transmitted using any appropriate medium including, but not limited to, wireless, wireline, optical fiber cable, radio-frequency (RF), etc., or any suitable combination of the foregoing.

Program/utility 40, having a set (at least one) of program modules 42, may be stored in memory 28 by way of example, and not limitation. Memory 28 may also have an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a consumer to interact with computer system/server 12; and/or any devices (e.g., network card, modem, etc.) that enable computer system/server 12 to communicate with one or more other computing devices. Such communication can occur via I/O interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

The inventors of the present invention have found that existing treatments for medical conditions that require specialized nutritional intake or diet are mainly focused on pharmaceutical compositions for the treatment of such conditions. Such medical conditions can include, for example, allergies/intolerances, Asthma, Celiac Disease, Colitis, Crohn's Disease, Dermatitis Herpetiformis, Diabetes, eating disorders (e.g., binge-eating disorder), High Cholesterol, Irritable Bowel Syndrome (IBS), and migraines. Existing solutions fail to fully address individual eating patterns and, as a result, fail to offer customizable control mechanisms to tailor a dietary treatment plan to the needs of an individual. While some people may choose to keep food diaries that record food intake and eating patterns, these too fail to provide patients with a forward-looking, individual control pattern beneficial to treating medical conditions that require specialized nutritional intake. As such, there is a gap between monitoring eating patterns and controlling such medical conditions on an individual level. Furthermore, current approaches lack any form of cognitive guidance or assistance recognizing nutritional intake symptoms of a medical condition and their severity on the individual level.

Accordingly, the inventors of the present invention have developed a system that quantifies food intake and creates a cognitive and customizable individual plan to alleviate medical conditions that require specialized nutritional intake or diet. More specifically, embodiments of the present invention assist patients though the process of eating habits correction by offering cognitive-behavioral therapy customized to the individual user. This cognitive and customizable individual plan teaches a patient to track his or her eating and change his or her unhealthy eating habits by providing the patient with curative strategies to react in difficult situations. For example, an embodiment of the present invention can detect a harmful eating event that includes nutritional substances that adversely affect the patient's medical condition and modify a patient's eating plan in real time to compensate for the event and/or minimize its effect on the patient, thereby cognitively customizing an eating plan to a patient immediately, as needed by the patient.

Embodiments of the present invention offer several advantages for assisting a patient with a medical condition that requires specialized nutritional intake or diet. For example, unlike previous solutions, embodiments of the present invention allow immediate revisions to an eating therapy plan, thereby allowing a patient to immediately be able to steer him or herself back onto the plan, even after a detrimental food intake event. Furthermore, embodiments are capable of using cognitive learning to profile ameliorative solutions that work best for a patient, and applying these solutions to different situations. This permits a patient to receive guidance on how to respond to a detrimental eating event that is specifically based on details of that event, even if those details differ from past events. Moreover, as treatments that incrementally encourage and support positive behaviors can have high success rates and long-lasting effects, embodiments offer a high likelihood of long term success. This is because embodiments offer persistent and cognitive eating routines for patients that dynamically compare and refer to the patient's current condition, thereby tracking a patient's responses to new routines over time and modifying these routines as needed for effectiveness with the patient.

Figure 2:
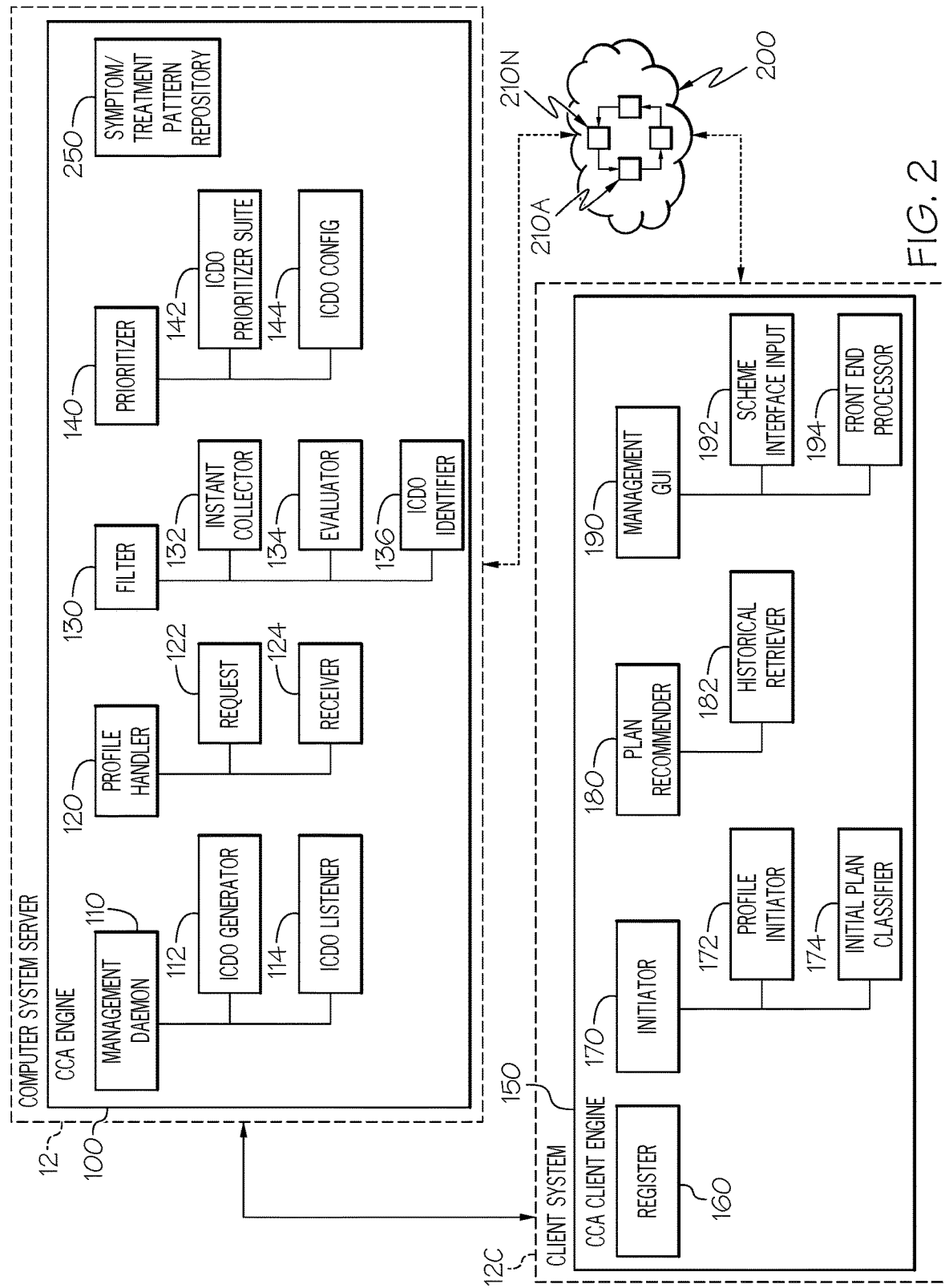
FIG. 2 shows a system diagram describing the functionality discussed herein according to illustrative embodiments.

Referring now to FIG. 2, a system diagram describing the functionality discussed herein according to an embodiment of the present invention is shown. It is understood that the teachings recited herein may be practiced within any type of computing environment, including, but not limited to, a networked computing environment (e.g., a cloud computing environment). A stand-alone computer system/server 12 and a stand-alone client computer system 12C are shown in FIG. 2 for illustrative purposes only. Referring additionally to FIG. 1, it should be understood that client computer system 12C can have the same type of components arranged in the same manner as shown in computer system/server 12, including external devices 14 and input devices, processing unit 16, bus 18, network adapter 20, I/O interfaces 22, display 24, and system memory 28 comprising RAM 30, cache memory 32, storage system 34, and/or program/utility 40 having a set of program modules 42. In the event the teachings recited herein are practiced in a networked computing environment, each client need not have a cognitive and customized assistant (CCA) engine 100 (hereinafter "system 100") or a CCA client engine 150 (hereinafter "system 150"). Rather, all or part of system 150 could be combined with system 100 and loaded on a server or server-capable device that communicates (e.g., wirelessly) with the clients to provide for treating a medical condition via individual customized cognitive guidance. Regardless, as depicted, system 100 is shown within computer system/server 12 and system 150 is shown with client computer system 12C. In general, system 100 and 150 can be implemented as program/utilities 40 of FIG. 1 on computer systems 12 and 12C, respectively, and can enable the functions recited herein.

Along these lines, systems 100 and/or 150 may perform multiple functions similar to a general-purpose computer. Specifically, among other functions, systems 100 and/or 150 can treat a medical condition via individual customized cognitive guidance in a networked computing environment. To accomplish this task, system 100 can include a set of components (e.g., program modules 42 of FIG. 1) for carrying out embodiments of the present invention. These components can include, but are not limited to management daemon 110, including interactive and customized diagnosis object (ICDO) generator 112 and ICDO listener 114; profile handler 120, including request 122 and 124 receiver; filter 130, including instant collector 132, ICDO evaluator 134, and ICDO identifier 136; prioritizer 140, including ICDO prioritizer suite 142 and ICDO configurer 144; and symptom/treatment pattern repository 250. To further accomplish this, system 150 can include a set of components (e.g., program modules 42 of FIG. 1) for carrying out embodiments of the present invention. These components can include, but are not limited to, register 160; initiator 170, including profile initiator 172 and initial plan classifier 174; plan recommender 180, including historical retriever 182; and management GUI 190, including scheme interface input 192 and front end processor 194. In some embodiments, system 100 and/or system 150 can also be in communication with, and dynamically receive data from, an internet of things (IoT) network 200 containing a set of IoT devices 210A-N.

Figure 3:
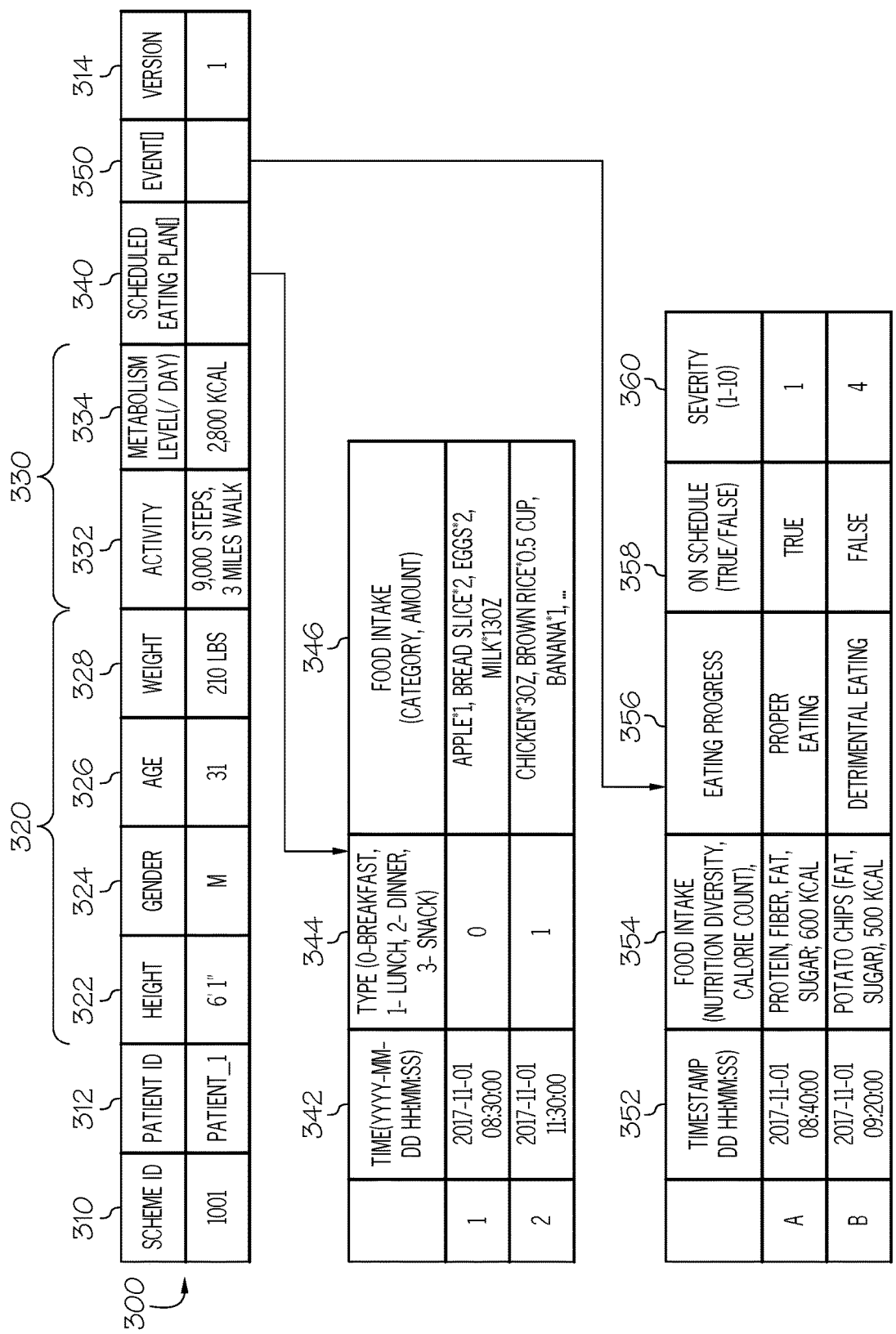
FIG. 3 shows creation of an interactive and customized diagnosis object (ICDO) according to illustrative embodiments.

Referring now to FIG. 3 in connection with FIG. 2, creation of an interactive and customized diagnosis object (ICDO) 300 is shown. Embodiments of the present invention utilize ICDOs 300. As such, before proceeding to describe further components and process of embodiments of the present invention, ICDO 300 will first be described in detail. ICDO 300 is a data structure that can contain various categories of data on a patient. The data included in ICDO 300 can include, but is not limited to, an identification 310 of a treatment plan scheme, a patient identification 312, a version 314 of ICDO 300, a physical description 320 of the patient, activity 330 of the patient, a scheduled eating plan 340 for the patient, and a set of actual food intake events 350 of the patient.

Treatment plan scheme 310 is a comprehensive strategy for treating a medical condition that requires specialized nutritional intake or diet in a patient. Due to differences in patients, such as body type, metabolism, disabilities, and lifestyle, different strategies may be better for some patients than others. For example, a younger patient may have a higher metabolism and/or engage in a greater amount of physical activity than an older patient.

Furthermore, a scheme 310 may change for a particular patient over time as the patient or medical professionals monitoring the patient choose to focus on different goals. For example, scheme 310 may initially focus on reducing adverse/detrimental eating events, and then later be replaced by a different scheme 310 that focuses on selecting food for consumption during mealtime that is healthier in light of the medical condition and more filling, or vice versa. Generally, an original treatment plan scheme is determined by a medical professional, such as a doctor, a nurse, a nutritionist, or a personal trainer and learned over time by system 100.

Physical description 320 of the patient can include a set of values describing any physical readings or observations that describe the patient. For example, this physical description can include a height 322, a gender 324, an age 326, and/or a weight 328 of the patient. Alternatively or additionally, physical description 320 of the patient can include any other readings or observations generally noted by a doctor or other healthcare professional, such as blood pressure, pulse, temperature, chronic medical complaints (e.g., joint ache, shortness of breath), current health state (e.g., patient currently has a cold/flu), etc. A patient can provide his or her permission to make such medical data available to system 100 and ICDO 300, as well as a doctor or other healthcare professional.

Activity 330 of the patient can include a set of values describing physical activity 332 (e.g., exercise, steps walked per day) of the patient, as well as the patient's metabolism 334. Metabolism 334 can include the number of Calories per day that the patient burns, given the physical activity 332 of the patient. In some embodiments, physical activity 332 and metabolism 334 can be static values that indicate the expected physical activity and corresponding burned Calories for the patient. These can be entered by a medical or other professional or automatically determined based on historic activity data. In some other embodiments, physical activity 332 and metabolism 334 can be dynamic values that reflect the patient's physical activity and Calories burned in real time. That is to say, the physical activity of the patient can be monitored in real time (using any of the IoT devices or monitoring techniques described further below) and an estimated number of Calories the patient is expected to metabolize that day determined dynamically based on this monitored activity. In some embodiments, activity 330 can also include daily nutritional minimums or maximums for the patient, based on the medical condition of the patient and the physical activity 332 of the patient. For example, a patient on a low sodium diet may have a maximum of 1500 mg of sodium per day, but, if the patient is engaged in strenuous physical activity that day, that maximum can be increased to 1800 mg of sodium for that day.

Scheduled eating plan 340 for the patient can include recommended daily food intake 346 for the patient, optionally organized by values representing recommended meal time 342 and/or type of meal 344 (e.g., breakfast, lunch, dinner, snack). Recommended daily food intake 346 can be described any number of ways. In some embodiments, recommended daily food intake 346 includes lists of specific types of food and quantity of such (e.g., 2 eggs, 12 oz. milk) be consumed per meal or day, which may contain any additional details to specify the food (e.g., 2 poached eggs, not fried; 12 oz. organic skim milk). In another embodiment, recommended daily food intake 346 includes a list of nutrients and/or Calories to be consumed per meal or day (e.g., 6 oz. protein/180 Calories). Recommended daily food intake 346 can initially be set by a medical or other professional during a machine learning phase, and subsequently automated during a run phase based on this machine learning.

The set of actual food intake events 350 of the patient include a list of actual food intake 354 by the patient. Each food intake event can be recorded separately, such that food intake events that are separated by a period of time (e.g., at least 10 minutes) are recognized as separate food intake events. In some embodiments, actual food intake 354 includes lists of specific types of food and quantity of such (e.g., 10 oz. potato chips) that the patient consumed at each event or per day, which may contain any additional details to specify the food (e.g., 10 oz. sour cream and onion potato chips). In another embodiment, actual food intake 354 includes a list of nutrients and/or Calories that the patient consumed at each event or per day (e.g., 500 Calories of fat and sugars, 1000 mg of sodium). Each actual food intake 354 can be associated with a timestamp indicating a time of actual food intake 354. In some embodiments, each actual food intake 354 can be associated with a value or other indicator that indicates whether that food intake event was in compliance (i.e., "proper eating") with a recommended food intake event from scheduled eating plan 340, or whether that food intake event was not (i.e., "detrimental eating"). Each actual food intake 354 can also or alternatively be associated with a value or other indicator that indicates whether that food intake event was on schedule or not (e.g., true or false, I/O) as compared with scheduled eating plan 340. Compliance can be gauged based on whether the quality and quantity of actual food intake 354 was within a tolerance (e.g., 10%) of the quality and quantity of food from a scheduled recommended food intake 346. For example, drinking 14 oz. of milk when only 13 oz. was recommended would still be within a 10% tolerance and therefore the food intake would be compliant, whereas eating 10 oz. of potato chips is not on the schedule and, therefore would be neither compliant nor on-schedule. Actual food intake 354 can be monitored in real time using any of the IoT devices or monitoring techniques described further below.

Severity 360 is a measure of a degree to which a quality or quantity of the patient's actual food intake 354 diverges from his or her scheduled recommended food intake 346. In some embodiments, this severity measurement can be a rating based on a proportion or quantity of deviation from the schedule. For example, for every so many Calories, grams of fat or sugar, or milligrams of sodium or cholesterol over the scheduled food intake, severity could be configured to increase by a measure of one on the rating scale (e.g., increasing to a severity of 4 in response to the consumption of 10 oz. of potato chips). Food intakes in compliance with the schedule could be rated a 0 or 1 on the scale (assuming a scale of 0-10 or 1-10). In some other embodiments, the rating scale could be increased based on a percentage over a maximum nutritional component of the patient's planned diet the unscheduled food intake brings the patient. For example, assuming a patient has a scheduled 1800 Calorie diet and consumes an extra 600 Calories, where a severity of 10 is preset as a 50% overage or more, then the 33% overage would be a severity level of 7. According to some embodiments, severity 360 can initially be provided by a medical or other professional during a machine learning phase, and subsequently automated during a run phase based on cognitive associations between the professional-provided ratings and the actual behavior of the patient.

ICDO 300 can be updated periodically (e.g., daily), such that, as will be discussed in more detail further below, a large plurality of ICDOs 300 can be created and stored, representing a progress of the patient over time and usable by system 100 to learn, through a computing learning algorithm, a nutritional treatment plan for the patient that can be cognitively modified in real time. ICDOs 300 can be numbered by version number 314 or by any other chronological numbering system to permit ICDOs 300 to be identified and ordered by age.

Figure 4:
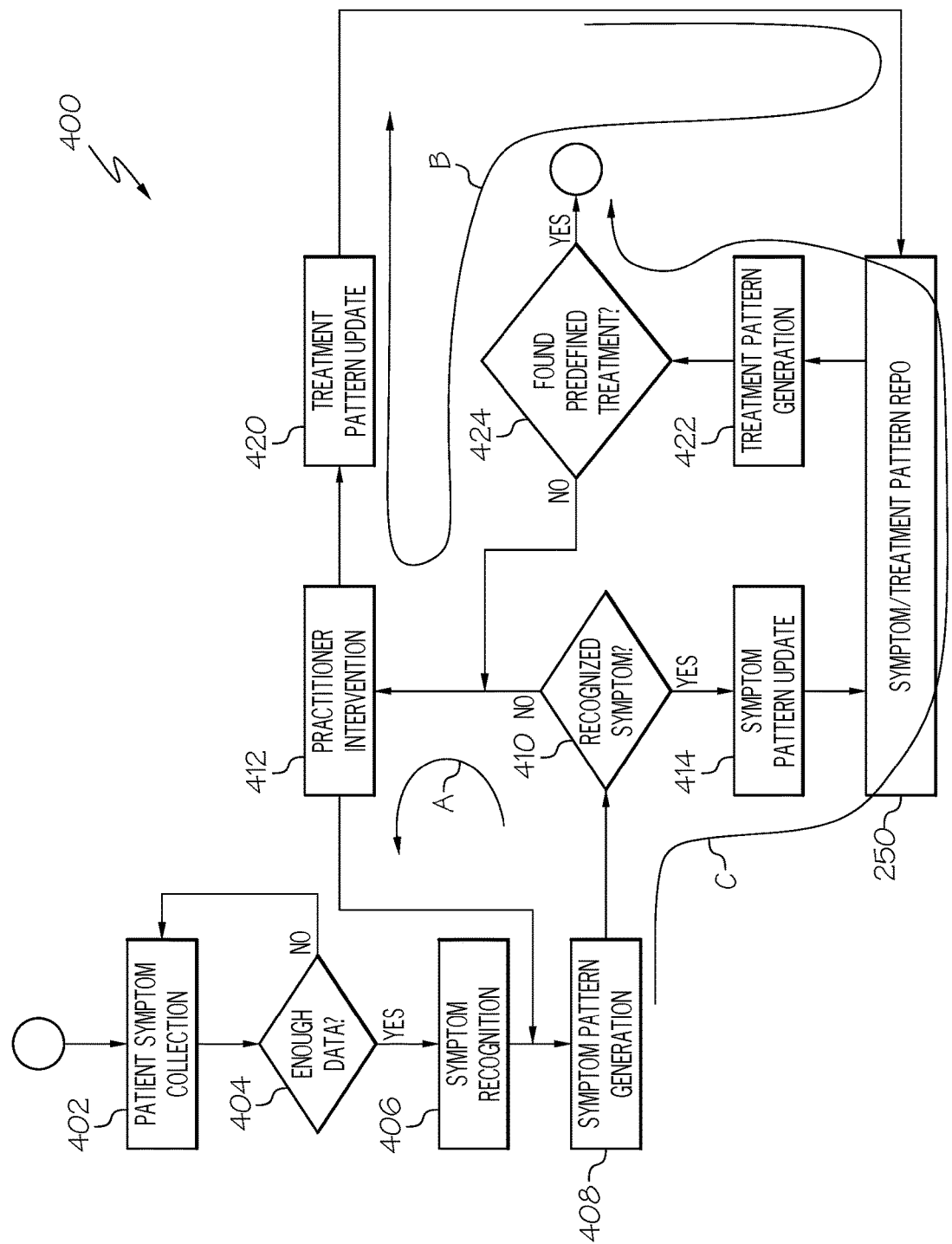
FIG. 4 shows a cognitive and customized assistant (CCA) process flow for developing a cognitive system/treatment pattern repository according to illustrative embodiments.

Referring now to FIG. 4 in connection with FIG. 2, CCA process flow 400 for developing a cognitive system/treatment pattern repository 250 is shown. In some embodiments, system/treatment pattern repository 250 can be preset with a list of predefined plans/schemes for treating a patient. One or more of these plans can then be linked to the individual patient according to the severity level of the patient symptoms and the patient's preferences. As used here, symptom can include an eating event that can have an adverse or detrimental effect on a patient with a medical condition necessitating a specialized nutritional intake or diet. As a patient receives guided treatment from a medical professional or other health professional, system/treatment pattern repository 250 can also store new diagnosis plans generated throughout these patient treatment sessions. The patient can opt in to sharing or otherwise providing his or her medical records, IoT data, biometric data, and food intake data to system 100, repository 250, and medical providers, such as medical professionals (e.g., doctors, nurses), nutritionists, or other health experts. The patient can further opt in to or otherwise permit data sharing between system 100, repository 250, and any medical providers assisting the patient with his or her medical treatment or therapy.

As can be seen in FIG. 4, CCA process flow 400 for developing cognitive system/treatment pattern repository 250 contains two loops: Loop A for patient symptom pattern training and Loop B for patient treatment pattern training. System 100 learns through professional (i.e., a medical professional, nutritionist, or other health expert) intervention 412 to recognize symptom patterns of a medical condition in Loop A and to recognize treatment patterns for those recognized symptoms in Loop B. During this process, system 100 builds symptom/pattern repository 250 for storing associations of learned symptom patterns with learned treatment patterns. Once a sufficient quantity of symptom and treatment patterns have been learned, system 100 can begin to enter automatic treatment Pathway C, in which system 100 automatically identifies symptoms and matches the symptoms to a treatment response by referring to symptom/treatment pattern repository 250. Should system 100 encounter a symptom that system 100 cannot recognize through symptom/treatment pattern repository 250, or should system 100 find no appropriate treatment for a detected symptom found in symptom/treatment pattern repository 250, system 100 can reenter Loop A or Loop B, respectively, to permit a professional to address the symptom or treatment, which system 100 then learns and stores in symptom/treatment pattern repository 250. In this manner, system 100 is an automated system capable of continuing learning, which can generate and refine patient symptom and treatment patterns over time.

Initiator 170, as performed by computer system 12C, defines an initial patient diagnosis schema to determine patient symptom severity. To accomplish this, register 160 collects initial static patient input (i.e., identifying information and symptoms) as variables at patient symptom collection 402. In embodiments where system 100 supports multiple patients, each patient and/or a medical/other professional acting on behalf of the patient, can individually register the patient at client computer system 12C associated with that patient and provide this initial symptom information. Register 160 also recognizes and defines an initial symptom severity level (e.g., 1 for low severity, 10 for high severity) for the patient. This symptom severity level recognition can be based on a symptom severity level input from a medical/other professional or based normalized historical data from other patients that associates particular medical condition symptoms with one or more severity levels.

Initiator 170 coordinates creation of an initial patient profile based on this first stage data collection. More specifically, profile initiator 172 creates an initial patient profile according to the patient input and recognition from register 160, while initial plan classifier 174 classifies a first stage plan/scheme stored in computer system 12C. Initial plan classifier 174 can also store or buffer future plans/schemes retrieved from computer system/server 12. Plan recommender 180 creates an initial recommended treatment based on the patient or medical/other professional inputted symptom information and the subsequent classification by initial plan classifier 174. In some embodiments, plan recommender 180 can include historical retriever 182, which can recognize a patient by his or her patient input and IoT tracking devices 210A-N. Historical retriever 182 can further recognize an individual patient's treatment preference and connect with system 100 to exchange tracking data from IoT devices 210A-N and ICDOs 300. Management GUI 190, which provides a user input interface (scheme interface input 192) and displays a graphic output of a dynamic treatment strategy (through front end processor 194) to the patient or professional, can be configured to display this recommended treatment plan (and any subsequently developed recommended plans) on a user interface of computer system 12C as customizable results. This permits the medical professional or other health professional to make further treatment plan selections according to recommender and generate a more customized initial plan.

In some embodiments, profile handler 120 of system 100 creates and maintains symptom/treatment pattern repository 250, which includes a profile repository, for each patient. Profile handler 120 can collect and store in repository 250 the above information from the initial on-demand symptom and medical background collection, including patient age, gender, hobbies/lifestyle, and medical history. Profile handler 120 can also, with patient consent, automatically collect and store in repository 250 information collected from IoT devices 210A-N of IoT network 200. Information collected by IoT devices 210A-N will be discussed in more detail further below. To accomplish these tasks, in some embodiments profile handler 120 includes request unit 122, which detects collected patient data and analyzes whether a sufficient quantity of information has been collected to identify a patient symptom and/or treatment by referring to repository 250. Profile handler 120 further includes receiver unit 124, which is a listening unit that collects the above and below discussed patient data and creates and maintains repository 250.

Figure 5:
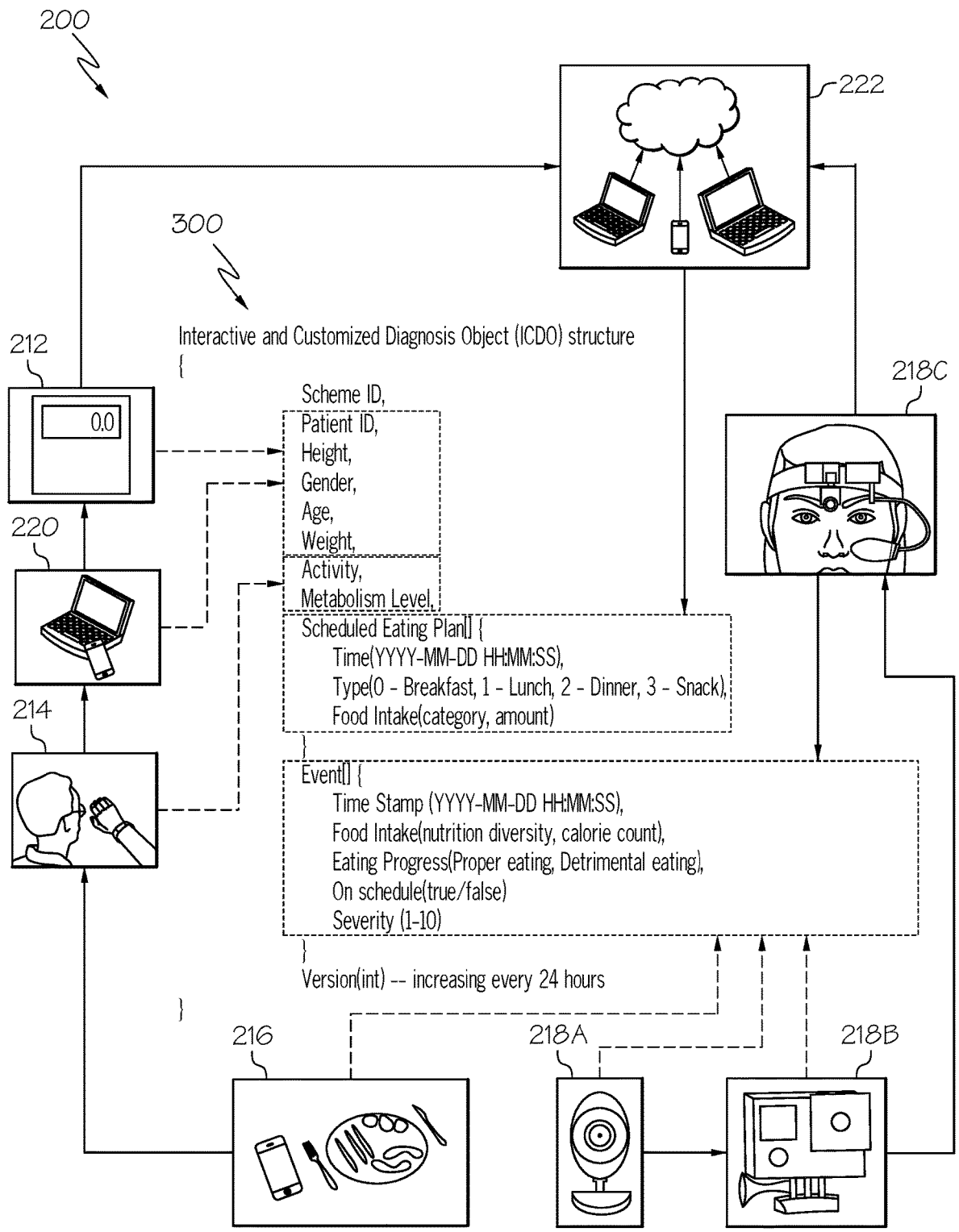
FIG. 5 shows population of an ICDO according to illustrative embodiments.

Referring now to FIG. 5 in addition to FIG. 2, FIG. 3, and FIG. 4, population of an ICDO 300 is shown. Management daemon 110, as performed by computer system/server 12, can provide the ICDO 300 structure (described above with respect to FIG. 3) which defines elements that are used to diagnose and match a patient with treatment. Furthermore, management daemon 110, as performed by computer system/server 12, can automatically create an initial ICDO 300 for the patient. More specifically, management daemon 110 creates and monitors ICDOs 300. In the case that an initial ICDO does not exist (as is the case when initiating a CCA process flow) or there is no up-to-date ICDO 300 for an existing patient, management daemon 110 requests ICDO generator 112 to create a new ICDO 300. It should be understood that, for each patient, ICDO generator 112 can create initial ICDO 300, as well as all subsequent ICDOs 300 for that patent based on patient input, tracking result, and individual preferences. Management daemon 110 also contains ICDO listener 114, which acts as an intermediate module between ICDO generator 112 and instant collector 132 (discussed below). ICDO listener 114 monitors new ICDOs 300 and verifies that an ICDO 300 for each patient is successfully created and up to date. If so, management daemon 110 transfers completed scheme objects 300 to instant collector 132 for population with current patient food intake data.

Instant collector 132 collects real-time information based on a profile of a patient for storage in the structure of ICDOs 300. To accomplish this, instant collector 132 can orchestrate continuous data collection from IoT network 200, which is formed from a plurality of data collection IoT devices 210A-N. Data collection IoT devices 210A-N can, with the patient's permission, track both biometric data and food intake data of the user and report this tracked information to instant collector 132. Data collection IoT devices 210A-N can include smart scale 212 for measuring a weight 328 of the patient and uploading it to IoT network 200; wearable 214 for tracking biometrics of the patient (e.g., physical activity 332, metabolism 334); smart plate 216 and camera devices 218A (e.g., web camera), 218B (e.g., action camera), and 218C (e.g., body-worn camera) for monitoring food intake events 350; and personal devices 220 of the patient and professional-controlled computer devices 222 for entering initial symptom and diagnosis information about the patient and receiving medical updates on the patient. As such, through communication with IoT network 200, instant collector 132 can provide continuous data, enabling system 100 to react to changes and make responsive modifications to scheduled eating plan 340 for the patient, as will be discussed in more detail further below.

Using IoT network 200 and/or IoT devices 210A-N, instant collector 132 can track patient food intake 354 at each food intake event 350. Using IoT devices 210A-N, one or more of the following food intake factors can be determined for the patient: food portion (e.g., number of ounces, number of standard servings); nutrition diversity (e.g., quantity or percentage of proteins, fats, carbohydrates, and other nutritional components, such as vitamins and minerals); quantity of substances that are potentially harmful to a patient in excess (e.g., sodium, cholesterol); and Calorie count (i.e., total Calories consumed at each event). To accomplish this, instant collector 132 can utilize any food identification technique presently known or later developed that can quantify food portion, nutrition diversity, potentially harmful substances, and/or Calories. For example, smart plates 216 are commercially available, and use a combination of photo recognition technology and artificial intelligence to identify food on a specialized smart plate IoT device and quantify the nutrition and Calorie content of that food. Similarly, or in addition, camera 218A-N can take pictures of food that the patient is about to consume (e.g., taken by the patient or automatically taken by an automatic camera in an eating area of the patient's home, office, etc.), and instant collector 132 can use an object recognition technique to quantify a nutrition and Calorie content of the photographed food.

Returning now to FIG. 4 in conjunction with FIG. 2 and FIG. 3, according to some embodiments of the present invention, system 100 can track a patient's initial eating pattern before creating an eating plan treatment for the patient. Instant collector 132, as performed by system/server 12, can monitor a status of a patient in real time via IoT network 200 associated with the patient. This allows system 100 to detect an actual event of the patient differing from a treatment schedule, as will be discussed in more detail below. As discussed above, through instant collector 132, system 100 can capture food intake events 350, including a food category, an amount, an eating frequency or time, and severity. These can then be compared to patient health condition (height, weight, age, gender, daily activity, metabolism, nutrition max/min). These factors are collected in initial ICDO 300. Instant collector 132 continues to collect food intake and symptom data on the patient, as well as other patient data included in ICDO 300 at 404 until sufficient data has been collected to permit recognition of a patient symptom at 406.

Management daemon 110 can automatically generate a set of updated ICDOs 300 for the patient by tracking a real-time status of the patient, wherein each individual ICDO 300 represents a treatment plan based on symptoms of the patient and progress of the patient. During data collection, symptoms (e.g., detrimental eating events that include nutritional material that is harmful to the patient's medical condition, such as high amount of sodium, cholesterol, sulfites, etc.) are recorded in one or more ICDOs 300. If initial data collection is required over multiple days, ICDO generator 112 can generate a plurality of ICDOs, one for each day. The set of ICDOs 300 are collected and analyzed by filter 130 and prioritizer 140 to find symptom patterns at 408. To accomplish this, in some embodiments filter 130 can include instant collector 132 to collect information from IoT devices 210A-N in real time for storage in the structure of ICDOs 300; ICDO identifier 136, which recognizes valid ICDOs and removes invalid ones (i.e., ICDOs 300 that are out of date or no longer approved by a professional as treatment sessions go on); and ICDO evaluator 134, which merges prioritized (see below) ICDOs 300 for a particular patient. By merging prioritized ICODs 300, ICDO evaluator 134 maintains an effectiveness of treatment sessions while balancing between patient configuration and professional strategies. In general, filter 130 can remove ICDOs 300 that are no longer valid in order to remove treatment schemes/plans that are not optimal for an individual patient. Filter 130 can be configured by a medical professional and/or by the patient to reflect individual treatment preferences of the patient. For example, a patient may indicate through scheme interface input 192 that he or she likes or dislikes a particular treatment technique.

To further accomplish the task of collecting and analyzing ICDOs 300, system 100 includes prioritizer 140, which is an overall control module that trims individual ICDOs 300 and creates a balance between treatment effectiveness and user comfort during runtime sessions to ensure high average treatment result for each patient. In some embodiments, prioritizer 140 includes ICDO prioritizer suite 142 and ICDO configuration 144. ICDO prioritizer suite 142 is a second level prioritizer within each patient's ICDOs 300. Multiple ICDOs 300 are generated for each patient during a treatment session, as ICDO 300 is configured to adapt to unscheduled food intake events 350 of the patient by creating a new ICDO 300 that reflects this event and compensates for it. As such, while previous ICDOs 300 during the same session are still valid (and reflect a patient's historical treatment overtime), they are not up to date, and, therefore, ICDO prioritizer suite 142 can keep track of the historic schemes in those ICDOs 300 and make automatic prioritizing changes in response to a relapse, such as when the patient has an unscheduled food intake event. ICDO configuration 144 is a customizable configuration file that prioritizer 140 can reference to maximize a patient's comfort during treatment session. ICDO configuration 144 allows a patient to set a treatment plan level and reasonably customize treatment strategies within parameters set by a medical professional.

Filter 130 and prioritizer 140, as performed by computer system/server 12, can generate a current ICDO 300 comprising a treatment schedule for a patient by combining a set of previous ICDOs 300 from the patient, wherein each ICDO 300 has a structure which defines elements that are used to diagnose a symptom of the patient and match the patient with a treatment. Returning to FIG. 4, at 410, if the symptom pattern (i.e., a detrimental eating event and the severity of the same) is recognized as a known symptom pattern, then the ICDO 300 containing a food intake event 350 showing the symptom pattern is added to symptom/treatment pattern repository 250 as an updated symptom pattern 414. However, if the symptom pattern is not recognized as a known symptom pattern at 410, then a medical professional or other health professional is requested at 412 (Loop A) to review the food intake event 350 showing the symptom pattern. The ICDO 300 containing the new symptom pattern can receive an identification of a symptom severity 360 from the medical professional or other health professional for that food intake event. For example, assume that a patient suffering from high cholesterol ate two cheeseburgers, a large fries, and large soda for lunch, when a veggie wrap, yogurt with fruit, and a glass of water had been scheduled. The professional can flag this as a harmful eating event in the current ICDO 300 and further enter that this is a harmful eating event of a severity seven. The professional-updated ICDO 300 can then be added to symptom/treatment pattern repository 250 as an updated symptom pattern 414, as this symptom pattern is now recognized.

The ICDO 300 containing the new symptom pattern can also receive a new treatment pattern responsive to the new symptom pattern from the medical professional or other health professional. This treatment is a modification to scheduled eating plan 340. Continuing the example above, assume that the health professional recommends that the patient replace his scheduled dressed baked potato dinner with a light salad to compensate for the burger and fries at lunch. The professional can create a new, current ICDO 300 in which the scheduled dinner meal is now a salad instead of a dressed baked potato. This treatment pattern (i.e., replace a high carbohydrate/cholesterol dinner with a light carbohydrate/cholesterol dinner to compensate for a high carbohydrate/cholesterol lunch) can be added to symptom/treatment pattern repository 250 as an updated treatment pattern 420 by entering the professional-updated ICDO 300 to symptom/treatment pattern repository 250, allowing this symptom pattern to now be recognized, as shown in Loop B.

Accordingly, when system 100 receives an ICDO 300 containing the known symptom pattern, that symptom pattern is recognized at 410, entered into symptom/treatment pattern repository 250, and a treatment sought at 422. If no treatment plan is found at 424, then the present ICDO 300 is sent to a medical professional or other health professional at 412 to request a treatment for the symptom pattern. The patient will continue to be monitored as the treatment plan is implemented to determine whether the treatment is effective or not and/or whether the patient prefers or does not prefer the treatment. If the treatment fails in either of these manners, a new treatment may be sought from the professional or a previously learned and preferred treatment may be substituted. Once a treatment pattern is known, any ICDO 300 containing a known symptom pattern that has a known treatment pattern can automatically return a treatment that modifies scheduled eating plan 340 to the patient, in response to a detrimental eating event, to correct for this event, as seen in Pathway C.

To accomplish this symptom and treatment pattern recognition, system 100 can apply analytics to any data received from IoT devices 210A-N, the patient, and/or the medical professional or other health professional to achieve dynamic customized ICDO management. Such analytic techniques can include harnessing IBM Watson APIs, or other cognitive analysis APIs, for intelligent grouping. (IBM Watson is a registered trademark of IBM Corporation.) Real-time patient statuses from IoT devices 210A-N and doctor/professional interventions are also used for this grouping process. For example, IBM speech-to-text services can be used to transcribe speech, such as feedback from patients, from various languages and audio formats to text that is transferred to create ICDOs 300. In another example, IBM Watson™ visual recognition services use deep learning algorithms to identify scenes, objects, and faces. Such visual recognition services can be used to identify foods consumed by a patient during food intake events 350. In yet another example, retrieve and rank services can be used to pre-process grouping results. In still yet another example, Watson Discovery services, which provide a cognitive search and content analytics engine that identifies real-time patterns, trends, and actionable insights to drive better decision-making, can be used to recognize symptom and treatment patterns across a vast number of ICDOs 300 stored in symptom/treatment pattern repository 250.

In any case, management daemon 110, as performed by computer system/server 12, can modify, in real time, a treatment schedule responsive to an event differing from a treatment schedule by adjusting the current ICDO 300 of the patient according to a learned set of rules to compensate for the differing event, the adjusting comprising exchanging one element of the treatment plan for a new element. This adjusted ICDO 300 contains a treatment scheme for the patient and can be adjusted to compensate for a detrimental eating event, such as an unscheduled food intake event. More specifically, when system 100 detects that the patient has deviated from his or her scheduled eating plan 340, as recorded in optimal ICDO 300, the system can measure a severity of this deviation by referencing historical, learned symptom patterns stored in symptom/treatment pattern repository 250. From the same symptom/treatment pattern repository 250, system 100 can retrieve a treatment associated with the severity of the medical condition symptom. For example, continuing the example from above, system 100 can now automatically exchange one element of the eating plan, such as a bowl of macaroni and cheese at dinner, for a new element, such as a lettuce wrap, in order to rebalance the patient's therapy and food intake, based on the learned rule to replace a high carbohydrate/cholesterol dinner with a light carbohydrate/cholesterol dinner to compensate for a high carbohydrate/cholesterol lunch. System 100 can then apply the retrieved treatment to optimal ICDO 300 to create a new version of optimal ICDO 300 that has a modified scheduled eating plan 340. This modified scheduled eating plan 340 of the new version of optimal ICDO 300 will permit the patient to compensate for his or her detrimental eating event, thereby mitigating the harm that is caused to the patient from such an event and the patient to train him or herself away from harmful eating behaviors. Management GUI 190, as performed by computer system/server 12C, can provide the modified treatment schedule to the patient in real time.

In addition to offering a modified scheduled eating plan 340 in optimal ICDO 300 to treat a patient's medical condition, system 100 can also, through system 150, provide a GUI to the patient or the patient's medical provider that presents patient progress. Patients and/or their medical providers can also extract records from saved ICDOs 300 to see if the patient has been improving or relapsing over time. Furthermore, in some embodiments, system 150 can be configured to provide visual or audio feedback to the patient. For example, if the patient initiates an unscheduled or unhealthy food intake event, system 150 can play an alert sound or display a warning. The sound or displayed visual can increase in intensity depending on the severity of the event. In contrast, if the patient follows scheduled eating plan 340, is eating within a threshold amount, or stops him or herself from an unscheduled food intake event, system 150 can play a positive sound (e.g., audio saying "good job!") or display a positive sign (e.g., a happy face). Additionally, in some embodiments, system 100 can compare horizontally a patient's per meal food intake across several days and provide positive or negative reinforcement feedback (sounds, visuals, rewards such as points) depending on whether the patient is improving or not.

Figure 6:
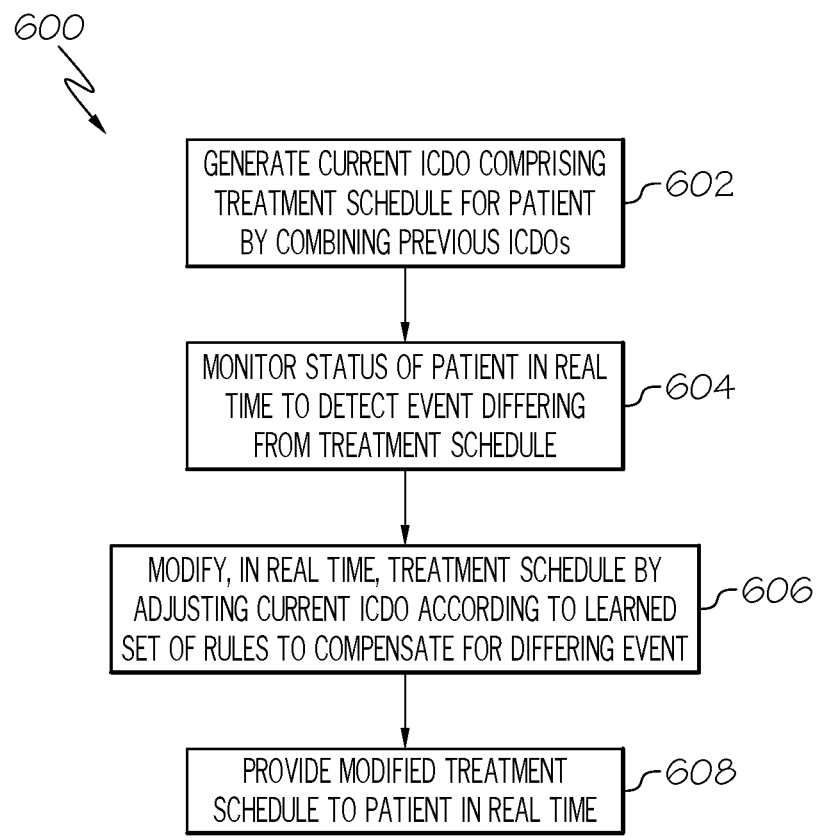
FIG. 6 shows a process flowchart for treating a medical condition via individual customized cognitive guidance according to illustrative embodiments.

As depicted in FIG. 6, in one embodiment, a system (e.g., computer system/server 12 (FIG. 1)) carries out the methodologies disclosed herein. Shown is a process flowchart 600 for treating a medical condition via individual customized cognitive guidance. Referring additionally to FIG. 2 and FIG. 3, at 602, filter 130 and/or prioritizer 140 can generate a current ICDO 300 comprising a treatment schedule for a patient by combining a set of previous ICDOs 300 from the patient, wherein each ICDO 300 has a structure which defines elements that are used to diagnose a symptom of the patient and match the patient with a treatment. At 604, instant collector 132 can monitor a status of the patient in real time via an internet of things network 200 associated with the patient to detect an actual event of the patient differing from the treatment schedule. At 606, management daemon 110 can modify, in real time, the treatment schedule responsive to the differing event by adjusting the current ICDO 300 of the patient according to a learned set of rules to compensate for the differing event, the adjusting comprising exchanging one element of the treatment plan for a new element. At 608, management GUI 190 can provide the modified treatment schedule to the patient in real time.

Process flowchart 600 of FIG. 6 illustrates the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Some of the functional components described in this specification have been labeled as systems or units in order to more particularly emphasize their implementation independence. For example, a system or unit may be implemented as a hardware circuit comprising custom VLSI circuits or gate arrays, off-the-shelf semiconductors such as logic chips, transistors, or other discrete components. A system or unit may also be implemented in programmable hardware devices such as field programmable gate arrays, programmable array logic, programmable logic devices, or the like. A system or unit may also be implemented in software for execution by various types of processors. A system or unit or component of executable code may, for instance, comprise one or more physical or logical blocks of computer instructions, which may, for instance, be organized as an object, procedure, or function. Nevertheless, the executables of an identified system or unit need not be physically located together, but may comprise disparate instructions stored in different locations which, when joined logically together, comprise the system or unit and achieve the stated purpose for the system or unit.

Further, a system or unit of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices and disparate memory devices.

Furthermore, systems/units may also be implemented as a combination of software and one or more hardware devices. For instance, program/utility 40 may be embodied in the combination of a software executable code stored on a memory medium (e.g., memory storage device). In a further example, a system or unit may be the combination of a processor that operates on a set of operational data.

As noted above, some of the embodiments may be embodied in hardware. The hardware may be referenced as a hardware element. In general, a hardware element may refer to any hardware structures arranged to perform certain operations. In one embodiment, for example, the hardware elements may include any analog or digital electrical or electronic elements fabricated on a substrate. The fabrication may be performed using silicon-based integrated circuit (IC) techniques, such as complementary metal oxide semiconductor (CMOS), bipolar, and bipolar CMOS (BiCMOS) techniques, for example. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor devices, chips, microchips, chip sets, and so forth. However, the embodiments are not limited in this context.

Any of the components provided herein can be deployed, managed, serviced, etc., by a service provider that offers to deploy or integrate computing infrastructure with respect to a process for treating a medical condition via individual customized cognitive guidance. Thus, embodiments herein disclose a process for supporting computer infrastructure, comprising integrating, hosting, maintaining, and deploying computer-readable code into a computing system (e.g., computer system/server 12), wherein the code in combination with the computing system is capable of performing the functions described herein.

In another embodiment, the invention provides a method that performs the process steps of the invention on a subscription, advertising, and/or fee basis. That is, a service provider, such as a Solution Integrator, can offer to create, maintain, support, etc., a process for treating a medical condition via individual customized cognitive guidance. In this case, the service provider can create, maintain, support, etc., a computer infrastructure that performs the process steps of the invention for one or more customers. In return, the service provider can receive payment from the customer(s) under a subscription and/or fee agreement, and/or the service provider can receive payment from the sale of advertising content to one or more third parties.

Also noted above, some embodiments may be embodied in software. The software may be referenced as a software element. In general, a software element may refer to any software structures arranged to perform certain operations. In one embodiment, for example, the software elements may include program instructions and/or data adapted for execution by a hardware element, such as a processor. Program instructions may include an organized list of commands comprising words, values, or symbols arranged in a predetermined syntax that, when executed, may cause a processor to perform a corresponding set of operations.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is apparent that there has been provided herein approaches for treating a medical condition via individual customized cognitive guidance. While the invention has been particularly shown and described in conjunction with exemplary embodiments, it will be appreciated that variations and modifications will occur to those skilled in the art. Therefore, it is to be understood that the appended claims are intended to cover all such modifications and changes that fall within the true spirit of the invention.

What is claimed is:

1. A method for treating a medical condition via individual customized cognitive guidance, the method comprising:
    generating a current interactive and customized diagnosis object (ICDO) comprising a treatment schedule for a patient by combining a set of previous ICDOs from the patient, wherein each ICDO has a structure which defines elements that are used to diagnose a symptom of the patient and match the patient with a treatment;
    monitoring a status of the patient in real time via an internet of things network associated with the patient that automatically collects and enters patient status data into a current ICDO of the patient, the current ICDO comprising set of individual treatment technique preferences of the patient machine learned from historical events of the patient that differed and that complied with historic treatment schedules of the patient, the internet of things network comprising at least one wearable sensor that transmits data to the current ICDO through the network, the internet of things network being configured to detect an actual event of the patient differing from the treatment schedule, the actual event compromising an action by the patient that deviates from the treatment schedule, wherein some of the previous ICDOs from the patient are deleted over time as the patient makes progress with treatment of the medical condition, leaving a set of currently valid ICDOs from which the current ICDO is derived;
    modifying, in real time, the treatment schedule responsive to the differing event by adjusting the current ICDO of the patient according to a learned set of rules derived from the set of currently valid ICDOs to compensate for the differing event, the learned set of rules comprising the set of individual treatment technique preferences of the patient and, the adjusting comprising exchanging one element of the treatment schedule for a new element compromising an action by the patient that brings the patient into alignment with a net effect of the initial treatment schedule, the exchanged element being optimized for treatment effectiveness, patient comfort, and historical successfulness based on the treatment technique preferences of the patient; and
    providing the modified treatment schedule to the patient in real time.

2. The method of claim 1, the method further comprising:
    creating automatically an initial ICDO for the patient;
    monitoring a real-time status of the patient via the internet of things network associated with the patient;
    generating automatically, responsive to the monitoring, a set of ICDOs updating the initial ICDO for the patient; and
    generating the set of rules customized to the patient from a set of symptom patterns and a set of treatment patterns learned from adjustments by a professional to the set of ICDOs during a machine learning phase.

3. The method of claim 2, the machine learning phase comprising:
    providing a configuration user interface for controlling and managing a real-time intervention service from a human user; and
    receiving a manual update to an ICDO of the set of ICDOs from a human who is monitoring symptoms of the patient and progress of the patient over time.

4. The method of claim 1, the learned set of rules comprising instructions to create a new treatment plan responsive to a progress of the patient not meeting a predetermined threshold.

5. The method of claim 1, wherein the actual event is an actual eating event and the treatment schedule is a scheduled eating plan and wherein the method further comprises:
    rating a severity level of the actual eating event of the user by comparing the actual eating event to a set of eating events in the scheduled eating plan for the patient; and
    updating the scheduled eating plan for the patient based on the severity level of the actual eating event.

6. The method of claim 1, further comprising:
    tracking patient activity, nutrition, and eating behavior over time;
    creating a diagnosis scheme to determine symptom severity, divided by behavior at each meal;
    defining a framework and related algorithms for supporting a real-time scheme filter;
    tracking historical symptom and treatment plan records against learned professional diagnoses; and
    developing a cognitive symptom and treatment pattern repository over time.

7. The method of claim 1, each ICDO comprising a physical description of the patient, activity of the patient, a scheduled eating plan for the patient, and a set of actual eating events of the patient.

8. The method of claim 7, wherein the scheduled eating plan for the patient comprises a list of a plurality of foods and portions the patient should eat at predetermined times during a day, and wherein the set of actual eating events of the patient comprises a list of a plurality of foods and portions the patient actually ate, an eating quantity rating, an eating schedule value, and an eating severity level value.

9. A computer system for treating a medical condition via individual customized cognitive guidance, the computer system comprising:
    a memory medium comprising program instructions;
    a bus coupled to the memory medium; and
    a processor, for executing the program instructions, coupled to a cognitive and customized assistant engine via the bus that when executing the program instructions causes the system to:
        generate a current interactive and customized diagnosis object (ICDO) comprising a treatment schedule for a patient by combining a set of previous ICDOs from the patient, wherein each ICDO has a structure which defines elements that are used to diagnose a symptom of the patient and match the patient with a treatment;

monitor a status of the patient in real time via an internet of things network associated with the patient that automatically collects and enters patient status data into a current ICDO of the patient, the current ICDO comprising set of individual treatment technique preferences of the patient machine learned from historical events of the patient that differed and that complied with historic treatment schedules of the patient, the internet of things network comprising at least one wearable sensor that transmits data to the current ICDO through the network, the internet of things network being configured to detect an actual event of the patient differing from the treatment schedule, the actual event compromising an action by the patient that deviates from the treatment schedule, wherein some of the previous ICDOs from the patient are deleted over time as the patient makes progress with treatment of the medical condition, leaving a set of currently valid ICDOs from which the current ICDO is derived;

modify, in real time, the treatment schedule responsive to the differing event by adjusting the current ICDO of the patient according to a learned set of rules derived from the set of currently valid ICDOs to compensate for the differing event, the learned set of rules comprising the set of individual treatment technique preferences of the patient and, the adjusting comprising exchanging one element of the treatment schedule for a new element compromising an action by the patient that brings the patient into alignment with a net effect of the initial treatment schedule, the exchanged element being optimized for treatment effectiveness, patient comfort, and historical successfulness based on the treatment technique preferences of the patient; and provide the modified treatment schedule to the patient in real time.

10. The computer system of claim 9, the instructions further causing the system to:
create automatically an initial ICDO for the patient;
monitor a real-time status of the patient via the internet of things network associated with the patient;
generate automatically, responsive to the monitoring, a set of ICDOs updating the initial ICDO for the patient; and
generate the set of rules customized to the patient from a set of symptom patterns and a set of treatment patterns learned from adjustments by a professional to the set of ICDOs during a machine learning phase.

11. The computer system of claim 9, the learned set of rules comprising instructions to create a new treatment plan responsive to a progress of the patient not meeting a predetermined threshold.

12. The computer system of claim 9, the actual event being an actual eating event and the treatment schedule being a scheduled eating plan, and the instructions further causing the system to:
rate a severity level of the actual eating event of the user by comparing the actual eating event to a set of eating events in the scheduled eating plan for the patient; and
update the scheduled eating plan for the patient based on the severity level of the actual eating event.

13. The computer system of claim 9, the instructions further causing the system to:
track patient activity, nutrition, and eating behavior over time;
create a diagnosis scheme to determine symptom severity, divided by behavior at each meal;
define a framework and related algorithms for supporting a real-time scheme filter;
track historical symptom and treatment plan records against learned professional diagnoses; and
develop a cognitive symptom and treatment pattern repository over time.

14. The computer system of claim 9, wherein each ICDO comprises a physical description of the patient, activity of the patient, a scheduled eating plan for the patient, and a set of actual eating events of the patient, and wherein the scheduled eating plan for the patient comprises a list of a plurality of foods and portions the patient should eat at predetermined times during a day, and wherein the set of actual eating events of the patient comprises a list of a plurality of foods and portions the patient actually ate, an eating quantity rating, an eating schedule value, and an eating severity level value.

15. A computer program product for treating a medical condition via individual customized cognitive guidance, the computer program product comprising a computer readable hardware storage device, and program instructions stored on the computer readable hardware storage device, to:
generate a current interactive and customized diagnosis object (ICDO) comprising a treatment schedule for a patient by combining a set of previous ICDOs from the patient, wherein each ICDO has a structure which defines elements that are used to diagnose a symptom of the patient and match the patient with a treatment;
monitor a status of the patient in real time via an internet of things network associated with the patient that automatically collects and enters patient status data into a current ICDO of the patient, the current ICDO comprising set of individual treatment technique preferences of the patient machine learned from historical events of the patient that differed and that complied with historic treatment schedules of the patient, the internet of things network comprising at least one wearable sensor that transmits data to the current ICDO through the network, the internet of things network being configured to detect an actual event of the patient differing from the treatment schedule, the actual event compromising an action by the patient that deviates from the treatment schedule, wherein some of the previous ICDOs from the patient are deleted over time as the patient makes progress with treatment of the medical condition, leaving a set of currently valid ICDOs from which the current ICDO is derived;
modify, in real time, the treatment schedule responsive to the differing event by adjusting the current ICDO of the patient according to a learned set of rules derived from the set of currently valid ICDOs to compensate for the differing event, the learned set of rules comprising the set of individual treatment technique preferences of the patient and, the adjusting comprising exchanging one element of the treatment schedule for a new element compromising an action by the patient that brings the patient into alignment with a net effect of the initial treatment schedule, the exchanged element being optimized for treatment effectiveness, patient comfort, and historical successfulness based on the treatment technique preferences of the patient; and
provide the modified treatment schedule to the patient in real time.

16. The computer program product of claim 15, the computer readable storage device further comprising instructions to:
create automatically an initial ICDO for the patient;
monitor a real-time status of the patient via the internet of things network associated with the patient;
generate automatically, responsive to the monitoring, a set of ICDOs updating the initial ICDO for the patient; and generate the set of rules customized to the patient from a set of symptom patterns and a set of treatment patterns learned from adjustments by a professional to the set of ICDOs during a machine learning phase.

17. The computer program product of claim 15, the learned set of rules comprising instructions to create a new treatment plan responsive to a progress of the patient not meeting a predetermined threshold.

18. The computer program product of claim 15, the actual event being an actual eating event and the treatment schedule being a scheduled eating plan, and the computer readable storage device further comprising instructions to:

rate a severity level of the actual eating event of the user by comparing the actual eating event to a set of eating events in the scheduled eating plan for the patient; and
update the scheduled eating plan for the patient based on the severity level of the actual eating event.

19. The computer program product of claim 15, the computer readable storage device further comprising instructions to:

track patient activity, nutrition, and eating behavior over time;

create a diagnosis scheme to determine symptom severity, divided by behavior at each meal;
define a framework and related algorithms for supporting a real-time scheme filter;
track historical symptom and treatment plan records against learned professional diagnoses; and
develop a cognitive symptom and treatment pattern repository over time.

20. The computer program product of claim 15, wherein each ICDO comprises a physical description of the patient, activity of the patient, a scheduled eating plan for the patient, and a set of actual eating events of the patient, and wherein the scheduled eating plan for the patient comprises a list of a plurality of foods and portions the patient should eat at predetermined times during a day, and wherein the set of actual eating events of the patient comprises a list of a plurality of foods and portions the patient actually ate, an eating quantity rating, an eating schedule value, and an eating severity level value.

\* \* \* \* \*